United States Patent [19]

Yesair

[11] Patent Number: 5,741,822
[45] Date of Patent: Apr. 21, 1998

[54] MIXED LIPID-BICARBONATE COLLOIDAL PARTICLES FOR DELIVERING DRUGS

[76] Inventor: David W. Yesair, 136 Main St., Byfield, Mass. 01922

[21] Appl. No.: 238,592

[22] Filed: May 5, 1994

Related U.S. Application Data

[62] Division of Ser. No. 908,442, Jun. 30, 1992, Pat. No. 5,314,921, which is a continuation of Ser. No. 567,243, Aug. 13, 1990, abandoned.

[51] Int. Cl.$^6$ .................................................. A61K 47/00
[52] U.S. Cl. ........................ 514/784; 514/786; 514/558; 514/560
[58] Field of Search .................. 514/558, 560, 514/784, 786

[56] References Cited

U.S. PATENT DOCUMENTS

| | | | |
|---|---|---|---|
| 3,169,094 | 2/1965 | Wretlind | 167/66 |
| 4,035,513 | 7/1977 | Kumano | 424/359 |
| 4,156,719 | 5/1979 | Sezaki et al. | 424/118 |
| 4,280,996 | 7/1981 | Okamoto et al. | 424/199 |
| 4,325,942 | 4/1982 | Taki et al. | 424/94 |
| 4,454,113 | 6/1984 | Hemker | 424/63 |
| 4,464,400 | 8/1984 | Kimura et al. | 424/365 |
| 4,874,795 | 10/1989 | Yesair | 514/725 |

FOREIGN PATENT DOCUMENTS

| | | |
|---|---|---|
| 0 245 871 | 11/1987 | European Pat. Off. |
| 2 427 100 | 12/1979 | France |
| 2 497 668 | 7/1982 | France |
| 1 492 824 | 8/1969 | Germany |
| 83/00294 | 2/1983 | WIPO |
| 86/05694 | 10/1986 | WIPO |

OTHER PUBLICATIONS

Muranishi, S. et al., "Improvements of Absolute Bioavailability of Normally Poorly Absorbed Drugs: Inducement of the Intestinal Absorption of Streptomycin and Gentamycin by Lipid-Bile Salt Mixed Micelles in . . . " *Int'l J. Pharmaceutics* 2: 101–111 (1979).

Muranishi, S. et al., "Absorption of 5-Fluorouracil from Various Regions of Gastrointestinal Tract in Rat. Effect of Mixed Micelles" *J. Pharm Dyn.* 2: 286–294 (1979).

Muranushi, N. et al., "Mechanism for the Inducement of the Intestinal Absorption of Poorly Absorbed Drugs by Mixed Micelles I. Effects of Various Lipid-Bile Salt Mixed Micelles . . . " *Int'l J. Pharmaceutics* 4: 271–279 (1980).

Taniguchi, K. et al., "Enhanced Intestinal Permeability to Macromolecules II. Improvement of the Large Intestinal Absorption of Heparin by Lipid-Surfactant Mixed Micelles in Rat" *Int'l J. of Pharamaceutics* 4: 219–228 (1980).

Serajuddin, A.T.M. et al., "In Situ Intestinal Absorption of a Poorly Water-Soluble Drug From Mixed Micellar Solutions of Bile Salt and Lipolysis Products in Rats" *Pharmaceut. Res.* (Received: Oct. 11, 1984; Accepted: Apr. 2, 1985) 221–224.

Yoshikawa, H. et al., "Potentiation of Enteral Absorption of Human Interferon Alpha and Selective Transfer into Lymphatics in Rats" *Pharmaceut. Res.* (Received: Jan. 25, 1985; Accepted: May 6, 1985) 249–250.

Muranishi, S., "Modification of Intestinal Absorption of Drugs by Lipoidal Adjuvants" *Pharmaceut. Res.* (1985) pp. 108–118.

Chem. Abst., 102: 154829p (1985) Ohashi et al.

Tso, P. et al. "The Importance of the Lysophosphatidylcholine and Choline Moiety of Bile Phosphatidylcholine in Lymphatic Transport of Rat" *Biochimica et Biophysics Acta*, 528: 364–372 (1978).

Tso, P. et al., "Formation and Transport of Chylomicrons by Enterocytes to the Lymphatics," *Am. J. Physiol.* 250 (6 Pt 1), 715–726 (Jun. 1986). Abstract only.

Staggers, J.E., "Lipid Digestion and Absorption in the Suckling Rat," Dissertation Abstracts International, (Sciences and Engineering), 44(10) : 3069 (218 pp) (1984). Abstract only.

*Primary Examiner*—Marianne M. Cintins
*Assistant Examiner*—M. Moezie
*Attorney, Agent, or Firm*—Wolf, Greenfield & Sacks, P.C.

[57] ABSTRACT

A composition is disclosed containing non-esterified fatty acids having 14–18 carbon atoms, monoglycerides which are monoesters of glycerol and fatty acids having 14–18 carbon atoms, lysophosphatidylcholine in which the fatty acid moiety has 14–18 carbon atoms and bicarbonate. The compositions can optionally also contain bile salts. These compositions form submicron size colloidal particles and can act as vehicles for transporting orally administered drugs, sources of calories in the form of readily absorbable fats and as particles for topical application to the skin. A method of making these particles is also described.

16 Claims, 6 Drawing Sheets

MIXED LIPID-BICARBONATE COLLOIDAL PARTICLES FOR DELIVERING DRUGS

RELATED APPLICATION

This application is a division of co-pending application Ser. No. 07/908,442 filed Jun. 30, 1992, now U.S. Pat. No. 5,314,921, which is a file wrapper continuation of Ser. No. 07/567,243 filed Aug. 13, 1990, now abandoned.

BACKGROUND OF THE INVENTION

Drug Absorption

Drugs must reach their targets selectively and controllably if their desired pharmacological activities are to be maximized. One approach to optimizing the activities of drugs is to control and sustain their delivery into the systemic blood circulation. Orally administered drugs are generally absorbed in the intestine. Such drugs undergo first pass clearance by the liver and small intestine; that is, they are converted by the intestine and the liver to pharmacologically inactive metabolites and/or are secreted into bile by the liver, either as drug or as active metabolites. As a result, the amount of an orally administered drug actually entering the systemic circulation can be much less than the amount administered. To ensure that effective quantities of such a drug will enter the circulation and reach the targeted site(s) in the body, larger quantities than actually needed must be administered and often must be given in several smaller doses, rather than one dose. Orally administered drugs also typically have poor bioavailability. For example, they may be adversely affected by the pH and the enzymatic activity of the stomach and intestine and may be poorly dissolved in the stomach and intestinal fluids.

There have been numerous attempts to address these problems and to improve the bioavailability of orally administered drugs. The efficacy of some drugs given orally has been improved by administering them with a triglyceride or neutral fat. Such fats represent an environment that is compatible with lipophilic drugs, i.e. that exhibit low aqueous solubility. Fats also enhance the stability of drugs which are unstable in the stomach and intestine. The end products of fat digestion are absorbed by the villi of the intestinal mucosa into a lymphatic vessel, the central lacteal; absorption occurs within a region of the intestine in which limited drug metabolism occurs. The absorbed fat is transported through the thoracic duct, the major lymphatic channel and is subsequently emptied into the blood; it is not carried in the portal blood, which goes to the liver, where first pass metabolism of drugs occurs.

The absorption of griseofulvin has been shown to be enhanced if the drug is co-administered with a high fat content meal or in an oil and water emulsion. Crounse, R. G., *Journal of Investigative Dermatology*, 37:529 (1961); Carrigan, P. J. and Bates, T. R., *Journal of Pharmacological Science*, 62:1476 (1973). If the hormone testosterone undecanoate is administered in a peanut oil solution, it is more biologically active than if it is administered in an aqueous micro-crystalline suspension. Coert, A. J. et al., *Acta Endocrinol*, 79:789 (1975); Hirschhauser, C. et al., *Acta Endocrinol*, 80:179 (1975). This effect is presumed to be due to absorption of the steroid via the thoracic lymph rather than the portal blood; in this way, first pass clearance by the liver is avoided.

Cholesterol, its esters as well as triglyceride constituents (e.g., fatty acids and monoglycerides) are absorbed via the thoracic lymph. The effects of some of these compounds, alone or in the presence of bile salts, upon absorption of some orally administered drugs have been evaluated. For example, oral administration of ubidecarenone, which is used for treating hypertension, in a mixture containing fatty acids having 12–18 carbon atoms and monoglycerides containing such fatty acids, resulted in somewhat greater absorption of the ubidecarenone than occurred after oral administration of the drug along (8.3% v. 2.3%). Taki, K. and Takahira, H., U.S. Pat. No. 4,325,942 (1982). If the steroid progesterone is administered orally in combination with cholesterol or its esters, good sustained biological activity can be obtained. This is believed to be due to the absorption of progesterone via the thoracic lymph and not via the portal circulation. Kincl, F. A., *Proceedings of the 6th International Congress of Pharmacology*, 5:105 (1975).

Yesair has evaluated the effect of fatty acids having 12–18 carbon atoms, monoglycerides of these fatty acids, and bile salts on the absorption of orally administered estradiol, which is an estrogenic hormone. Yesair, D. W., PCT WO 83/00294 (1983). The mole ratio of fatty acids:monoglycerides:bile salts evaluated ranged from 10:1:1, 1:1:10 or 1:10:1. The preferred ratio was stated to be 2:1:2, which is similar to the micellar composition resulting from the enzymatic digestion of triglycerides in the intestine, which occurs in the presence of bile salts and calcium ions. When excess bile salts are present, estradiol incorporated into the 2:1:2 composition can migrate or partition into a bile salt-enriched micellar solution. This migration or partitioning of estradiol occurred prior to absorption of the drug, as shown by the fact that the initial concentrations in plasma of estradiol are initially greater than those in lymph. In addition, about 25–50% of the estradiol administered in the composition was co-absorbed with the lipid constituents and entered the systemic circulation via the thoracic lymph.

The presence of bile salts, which are absorbed in the ileum (and not in the jejunum, as is most fat) compromised the co-absorption of estradiol with fat by enhancing the migration of the drug from fat to the bile salt micelle. Phosphatidylcholine was used in an effort to maintain the estradiol within the micellar composition in which fatty acids:monoglycerides:bile salts occurred in a 2:1:2 molar ratio. In the presence of excess bile salts, about 60% of the estradiol incorporated into the 2:1:2 micellar composition remained associated with it when phosphatidylcholine was not present. Under the same conditions, about 70–75% of the estradiol remained in the composition when phosphatidylcholine was used. Addition of phosphatidylcholine for this purpose, however, results in an increased size of the delivery system. Size is an important parameter in the absorption of lipid micelles and this effect of phosphatidylcholine might interfere with co-absorption of the drug with the lipids. In addition, excess phosphatidylcholine has been shown to reduce lipid absorption. Ammon, H. V., et al., *Lipids*, 14:395 (1979); Clark, S. B., *Gastrointestinal Physiology*, 4:E183 (1978).

Others have also described the effects of the presence of bile salts in lipid formulations used for co-absorption of drugs. Wilson, T. H., In: *Intestinal Absorption*, Saunders, (1962); Lack, L. and Weiner, I. M., *American Journal of Physiology*, 240:313, (1961); H. V. Ammon et al., *Lipids*, 14:395 (1979). For example, little difference in the absorption of 5-fluorouracil (5FU) in the stomach or small intestine was evident when the 5FU was administered alone or in a mono-olein/sodium taurocholate mixed micelle formulation. 5FU absorption in the large intestine was greater when the drug was administered in the formulation than when it was administered alone. Streptomycin is poorly absorbed from the intestine. Muranushi and co-workers report that mixed micelles, composed of bile salts, monoolein or unsaturated fatty acids, did not improve the absorption of streptomycin from the small intestine but markedly enhanced the absorption from the large intestine. The enhancement in the large intestine was attributed mostly to the alteration of the mucosal membrane permeability by monoolein or unsaturated fatty acids. In contrast, mixed micelles of bile salts and saturated fatty acids produced only a small enhancement in streptomycin absorption even from the large intestine. Muranushi, N. et al., *Journal of Pharmaceutics*, 4:271 (1980). Taniguchi et al report that mono-olein/taurocholate or oleic acid/taurocholate promotes the absorption of heparin, which is poorly absorbed when administered alone. Taniguchi, K. et al., *International Journal of Pharmaceutics*, 4:219 (1980). Absorption of heparin from the large intestine was twice that which occurred from the small intestine. The concentration of heparin in the mixed micelle to produce the potentiation in the large intestine was approximately one-fourth that required in the small intestine.

In U.S. Pat. No. 4,156,719, Sezoski and Muranishi describe a micelle solution for rectal administration of water-soluble drugs that are poorly absorbed. The composition consists of fatty acids having 6–18 carbons, and/or mono- or diglycerides having the same type of fatty acids; a bile salt or other non-ionic surface activity agent; and water. A lysophosphatidylcholine moiety can be substituted for the fatty acids and mono- or diglycerides. Absorption of streptomycin and gentamycin from the rectum and large intestine is reported to be comparable when the drug is administered in a bile salt:mixed lipid micelle. Similar formulations were not effective in increasing absorption in the duodenum. Muranushi, S. et al., *International Journal of Pharmaceutics*, 2:101 (1979). Absorption of the two drugs via the rectum and large intestine was markedly greater than that of a comparable dose administered duodenally, even when the mixed lipid micelle concentration administered duodenally was four times that administered via the other routes.

In a patent to the present inventor (U.S. Pat. No. 4,874,795, Yesair) it was shown that a lipid composition with specific lipid components in a prescribed relationship to each other was effective in delivering drugs to the systemic circulation. The lipid composition included fatty acids having 14–18 carbon atoms, monoglycerides with a fatty acid moiety having 14–18 carbon atoms, and lysophosphatidylcholine with a fatty acid moiety having 14–18 carbon atoms. The fatty acid to monoglyceride molar ratio could range from 2:1 to 1:2 and the mole percent of lysophosphatidylcholine could range from 30.0 to 1.0 when expressed as the mole percent of the total lipid composition. This lipid composition was shown to effectively transport drugs to the systemic circulation when they were incorporated into the lipid composition. The lipid composition also was shown to serve as a source of calories by virtue of its inherent fatty acid content that could be metabolized in an individual's body.

Nutrition

Caloric requirements for individuals are primarily a function of body composition and level of physical activity. Medically compromised, aged and physically stressed individuals often have limited body fat. Consequently, energy (caloric) needs will be satisfied mainly from exogenous sources.

Physical activity uses muscle and the energy requirements of all muscles, including the heart, are met primarily as a result of oxidation of fatty acids, from dietary fat or mobilized adipose fat. Adipose fat can, as noted, be minimal and therefore efficient absorption of fat can be an important consideration in satisfying the energy demands of the medically infirm, the aged and the physically active.

Fat absorption can be compromised in many circumstances. For example, in cystic fibrosis, a disorder of exocrine glands, there is a deficiency of pancreatic enzymes, bile salts and bicarbonate ions. *Nutrition Reviews*, 42:344 (1984); Ross, C. A., *Archives of Diseases of Childhood*, 30:316 (1955); Scow, R. O. E., *Journal of Clinical Investigation*, 55:908 (1975). Fat absorption in cystic fibrosis patients can be severely affected and 30 to 60 percent of ingested fat can be malabsorbed. The malabsorption and resulting steatorrhea are generally not successfully handled by the oral administration of pancreatic lipase. In an effort to control the steatorrhea, the patient may consume less fat than desirable for good health.

Fat absorption can be compromised under stressful conditions and the generally accepted way of addressing this problem has been to reduce fat consumption. This approach can result in both acute and chronic medical problems. These problems might be avoided, or at least minimized, if a readily absorbable source of fat could be made available.

At the present time, there is a need for a more efficient method of transporting orally administered drugs to the systemic circulation. This need is particularly important for individuals with impaired oral intake, intestinal absorption or diminished transport capacity. At the same time, there is a need for a more efficient oral administration of calorically rich substances, especially to individuals with acute energy requirements. The achievement of such increased efficiencies would promote more effective drug therapies and nutritional stability.

SUMMARY OF THE INVENTION

This invention relates to compositions for providing at least one drug or for providing readily absorbable calories to an individual. The basic composition of the present invention is comprised of: (1) at least one non-esterified fatty acid having 14–18 carbon atoms, (2) at least one monoglyceride which is a monoester of glycerol and a fatty acid having 14–18 carbon atoms, (3) lysophosphatidylcholine in which the fatty acid moiety has 14–18 carbon atoms, and (4) bicarbonate. An optional fifth component of the composition is bile salts, which can be added to the other four components of the basic composition. The composition of the present invention is in the form of mixed lipid colloid particles, since they form a colloidal suspension in an aqueous environment. In those instances in which components (1) through (4) are present in a composition, the composition is referred to as a mixed lipid-bicarbonate composition (i.e., a mixed lipid-bicarbonate colloid) and in those instances in which components (1) through (4) plus bile salt are present, the composition is referred to as a mixed lipid-bicarbonate-bile salt composition (i.e., a mixed lipid-bicarbonate-bile salt colloid). The bile salt component is added when it is desired to further reduce the size of the particulate form of the basic composition from its inherent colloidal size.

In both types of compositions, the non-esterified fatty acid and the esterified fatty acid moieties of the monoglycerides and lysophosphatidylcholine can be saturated or unsaturated. If the non-esterified fatty acids in the composition are saturated, sufficient quantities of divalent cations (approximately one-half the molar amount of the fatty acids), such as calcium ions, can optionally be added to form non-esterified fatty acid salts. These non-esterified fatty acid salts would then form the non-esterified fatty acid portion of the composition.

The non-esterified fatty acids and the monoglycerides are present in the composition in a molar ratio of between about 2:1 and about 1:2 (non-esterified fatty acid:monoglyceride). Taken together, the non-esterified fatty acids plus monoglycerides comprise from about 70.0 mole percent to about 99.0 mole percent of the total lipid composition. The lysophosphatidylcholine therefore comprises from about 30.0 mole percent to about 1.0 mole percent of the total lipid composition.

The components of the composition of the present invention, namely the fatty acids, monoglycerides, lysophosphatidylcholine, bicarbonate, and optionally, bile salts, can be combined to form a mixture before being placed in an aqueous environment. Preferably, however, the fatty acid, monoglyceride and lysophosphatidylcholine lipids of the basic composition are mixed together and then placed in an aqueous environment for the subsequent addition of bicarbonate, and optionally, bile salts. In either instance, following placement of the mixed components in the aqueous environment, the composition is further processed to form the colloidal particles. For example, it can be subjected to a shearing operation, mixed or stirred, sonicated or otherwise subjected to an appropriate force. To achieve these colloidal particles, the lysophophatydylcholine concentration of the lipid components (i.e., the sum of the concentrations of the individual lipid components) should be at least about 0.1 mM to ensure stable, mixed lipid particle formation.

The inclusion of bicarbonate in the basic mixed lipid-bicarbonate composition provides a means for controlling the size of the colloidal particles formed as a result of the intermolecular forces between the components of the composition in an aqueous environment. When the molar ratio of bicarbonate to the lysophosphatidylcholine in the total lipid is about 1.4:1 or less, the mixed lipid-bicarbonate colloidal particle size is approximately 120 nm or larger. When the molar ratio of bicarbonate to the lysophosphatidylcholine in the total mixed lipid increases from about 2:1 to about 7:1, the mixed lipid-bicarbonate colloidal particle size decreases from approximately 120 nm to approximately 70 nm in direct relationship to the increase in molar ratio of bicarbonate to lysophosphatidylcholine in the total mixed lipid. If the molar ratio of bicarbonate to lysophosphatidylcholine in the total mixed lipid is increased beyond about 7:1, there is no further decrease in mixed lipid-bicarbonate colloidal particle size.

When bile salts are additionally incorporated into the lipid-bicarbonate composition, the resulting mixed lipid-bicarbonate-bile salt colloidal particle size is smaller than the mixed lipid-bicarbonate colloidal particle size. For example, if the molar ratio of bicarbonate to the lysophosphatidylcholine in the total mixed lipid is at least about 7:1 and the molar ratio of bile salt to the lysophosphatidylcholine in the total mixed lipid is at least about 10:1, the mixed lipid-bicarbonate-bile salt colloidal particle size is about 10 nm or less.

The compositions of this invention are designed to promote uptake of the mixed lipid colloid of the lipid formulations into the mucosa of the small intestine, subsequent synthesis into chylomicrons, translocation of the chylomicrons to the thoracic lymph and eventual transport to the systemic circulation (i.e., the blood stream). The compositions which are the subject of this invention have several characteristics which will promote rapid and quantitative absorption of lipids in the small intestine and transport of lipids via the lymphatic system. First, the mole ratio range described for the fatty acids and monoglycerides is optimal for their absorption in the jejunum. Second, the unsaturated fatty acids or saturated fatty acid-calcium salts included in the compositions have been shown to be maximally absorbed and preferentially transported via the thoracic lymph rather than via the portal blood. Third, the compositions contain lysophosphatidylcholine which enhances translocation of the lipid particles as chylomicrons into the thoracic lymph. Fourth, the reduction in size of the lipid particles allows the existence of more particles per unit volume and promotes ease of mass transport of the individual particles. This reduction in size of the particles also allows a higher concentration of organized lipid particles to exist in an aqueous environment.

The mixed lipid compositions which are the subject of this invention can serve as a transport vehicle for enhanced uptake and bioavailability of a drug or drugs. Drugs are broadly defined here as any chemical agents or chemical substances which affect living processes. These chemical substances can become integrally incorporated into the basic lipid particles. Examples of substances which can be incorporated into the basic composition of this invention are drugs administered for diagnostic, therapeutic or preventive purposes, lipophilic pro-drugs, bioactive peptides and other xenobiotics. Other such substances include vitamins, e.g., fat-soluble vitamins, and other like materials of metabolic or nutritive value. The enhanced uptake occurs because the substance incorporated into the compositions of this invention is absorbed together with the lipids and subsequently enters the systemic circulation via the lymphatic system. The substance is absorbed more rapidly and more completely than it otherwise would be because first pass clearance by the liver is avoided. Thus, more of the absorbed dose enters the blood and is available to reach target sites within an individual's body than would be available if the mixed lipid-bicarbonate formulations were not used.

The subject compositions can also serve as highly concentrated sources of readily absorbable fat, which can be used, for example, by those individuals in need of a calorically dense dietary component. When used in this manner, the compositions of the present invention generally do not include a drug and are comprised of the nonesterified fatty acids, monoglycerides and lysophosphatidylcholine. They can, for example, include a fat soluble vitamin.

The subject compositions also provide stable mixed lipid colloids that protect incorporated drugs from, for example, enzymatic and chemical degradation in the stomach and upper intestine. In addition, the inherent stability of the lipid components of the compositions make the compositions stable over extended periods of time and thus can serve as stable delivery vehicles for the substances incorporated into the mixed lipid-bicarbonate formulations.

The subject mixed lipid compositions can be produced according to the following method: In the preferred embodiment, the method includes the following steps: First, the following components are combined in a non-aqueous environment: (1) at least one non-esterified fatty acid having 14–18 carbon atoms, (2) at least one monoglyceride which is a monoester of glycerol and fatty acid having 14–18 carbon atoms, and (3) lysophosphatidylcholine in which the fatty acid moiety has 14–18 carbon atoms. The non-esterified fatty acids, monoglycerides and lysophosphatidylcholine are mixed together in molar ratios as described above and then placed in an aqueous environment containing the bicarbonate component. Second, the mixed lipid composition is subjected to shearing forces of sufficient energy and for sufficient time for lipid particles of uniform size to form. The shearing forces produce cavitation of the aqueous environment containing the lipid and bicarbonate components such that these components segregate into particles. The results of this shearing operation are mixed lipid-bicarbonate colloidal particles of a homogeneous, uniform size.

The shearing forces may be applied as the bicarbonate is being added to the mixed lipid-aqueous mixture or they can be applied after the bicarbonate has been added to achieve a specified molar ratio of bicarbonate to total mixed lipid. In either case, the same mixed lipid-bicarbonate colloidal particle size results.

The same method is used to produce the mixed lipid-bicarbonate-bile sale compositions of the present invention. Again, the bile salt can be added before or during the shearing operation. The same mixed lipid-bicarbonate-bile salt colloidal particle size is achieved in either occurrence.

The bicarbonate and bile salt can be added to the lipid mixture in the aqueous environment either simultaneously or sequentially. The order in which they are added is not critical. The same uniform mixed lipid-bicarbonate-bile salt colloidal particle size is achieved regardless of which order the bicarbonate and bile salt are added. To achieve the 10 nm or less mixed lipid-bicarbonate-bile salt colloidal particle size, the proper molar ratios of bicarbonate to total mixed lipid and bile salt to total mixed lipid must be attained before the final Shearing operation.

The above identified lipid particles can also be formed when biologically compatible surfactants, such as TWEEN 80, are added to the above formulations. The addition of such surfactants does not impede the formation of the mixed lipid-bicarbonate or mixed lipid-bicarbonate-bile salt colloidal particles.

A drug or drugs can be administered to an individual by oral administration of a mixed lipid-bicarbonate composition of the present invention in which the drug (or drugs) is incorporated. Likewise, calories in the form of fatty acids, monoglycerides or lysophosphatidylcholine can be delivered to individuals by orally administering the above mixed lipid-bicarbonate compositions. In either case, bile salts can optionally be a component of the mixed lipid bicarbonate composition to form mixed lipid-bicarbonate-bile salt compositions that can be administered orally to an individual.

DETAILED DESCRIPTION OF THE INVENTION

Figure 1:
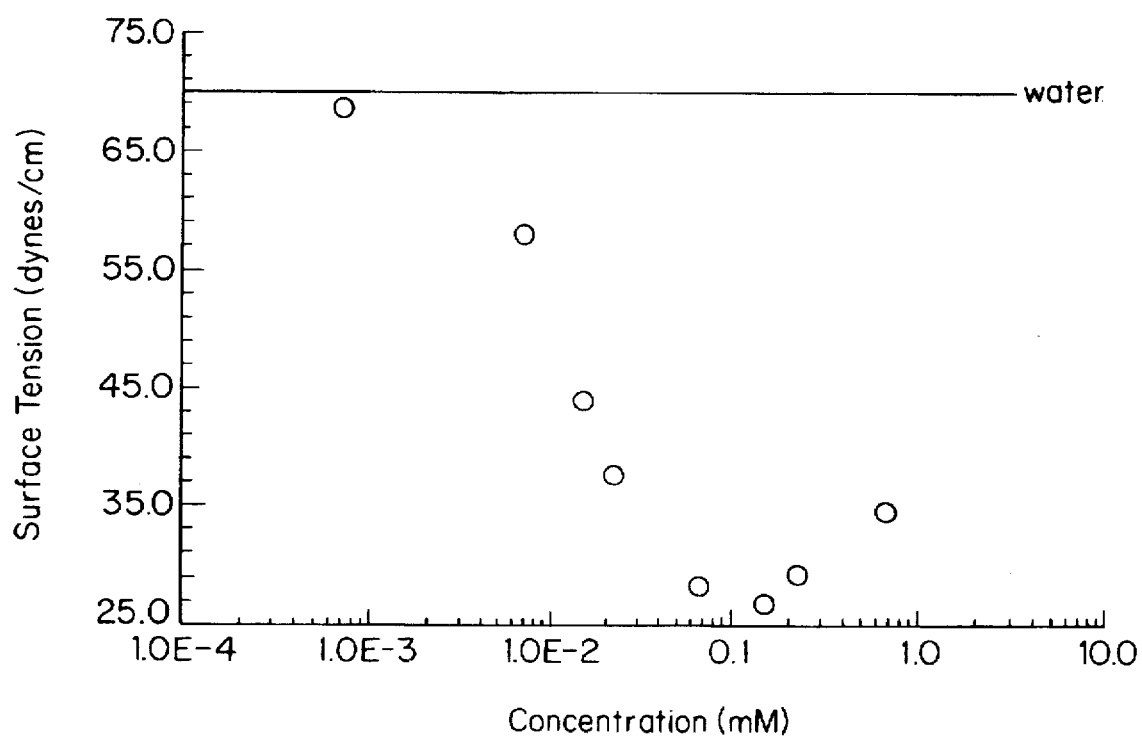
FIG. 1 is a graph showing the relationship between the surface tension of the mixed lipid formulation and the molar concentration of the lysophosphatidylcholine (and mixed lipids) in the mixed lipid formulation.

The composition of the present invention is comprised of non-esterified fatty acids, monoglycerides of those fatty acids, lysophosphatidylcholine having those fatty acids as their fatty acid moiety, and bicarbonate. The selection of the components of the subject composition is based on the absorption and transport characteristics of the fatty acids, the contribution of lysophosphatidylcholine to solubilization of drugs in the lipid composition, the properties of bicarbonate that allow stable, submicron size lipid-containing particles to exist and to translocation of absorbed fat into the lymph (rather than into the portal circulation).

Absorption of saturated fatty acids has been shown to be inversely related to the number of carbon atoms in the fatty acid. For example, absorption of decanoic (10:0, which denotes chain length and degree of unsaturation) is almost quantitative. For lauric (12:0), it is more than 95%; for myristic (14:0), 80–90%; for palmitic (16:0), 65–70% and for stearic (18:0), 30–45%. Absorption of unsaturated fatty acids into lymph (e.g., linoleic 18:2) have been shown to be more rapid and to a greater extent than are saturated fatty acids. Taniguchi, K., *International Journal of Pharmaceutics*, 4:219 (1980).

Transport of absorbed fatty acids via the lymph (and not in the portal circulation) varies greatly. That is, a much larger percentage of absorbed unsaturated fatty acids has been shown to be carried in the lymph than is the case for saturated fatty acids. About 85% of unsaturated fatty acids has been shown to be carried in the lymph. Miura, S. et al., *Keio Journal of Medicine*, 28:121 (1979). The amount of these absorbed fatty acids being carried in the lymph is also inversely related to chain length: 68–80% for myristic; 85% for palmitic and stearic.

If saturated fatty acids are included in the composition of this invention, they can be included as calcium salts or salts of another cation. This is true because the enzymatic hydrolysis of triglycerides, which releases saturated fatty acids, favors their calcium soap formation. Tak, Y. A. and Grigor, M. R., *Biochimica Biophysica Acta*, 531:257 (1978).

Translocation of absorbed fat into the lymph has been shown to require lysophosphatidylcholine. The rate, but not the magnitude, of the translocation of absorbed fat is apparently related to the fatty acid moiety of the lysophosphatidylcholine. For example, oleoyl lysophosphatididylcholine results in a 100% increase in triglyceride and phospholipid in lymphatic transported fat when compared with the effects of a lysophosphatidylcholine derived from a phosphatidylcholine composed mainly of saturated fatty acids (e.g., palmitic, C16:0; stearic, C18:0). Incorporating an unsaturated lysophosphatidylcholine into the compositions of this invention will enhance the translocation of the absorbed lipids and the co-absorbed drugs or other substances. In addition, lysophosphatidylcholine plays a role in the solubilization of some drugs (i.e., its presence enhances the solubility of the drugs in the compositions).

Examples of unsaturated fatty acids which can be used in the composition of this invention are:

| palmitoleic | $C_{16}H_{30}O_2$ | 16:1 |
| oleic | $C_{18}H_{34}O_2$ | 18:1 |
| linoleic | $C_{18}H_{32}O_2$ | 18:2 |
| linolenic | $C_{18}H_{30}O_2$ | 18:3 |

Examples of saturated fatty acids which can be used in the subject composition are:

| myristic | $C_{14}H_{28}O_2$ | 14:0 |
| palmitic | $C_{16}H_{32}O_2$ | 16:0 |
| stearic | $C_{18}H_{36}O_2$ | 18:0 |

The unsaturated and saturated fatty acids can be present individually or in combination. That is, the fatty acid constituents of one or more of the lipid components (fatty acid, monoglyceride and lysophosphatidylcholine) can be identified or they can be a mixture of the unsaturated and/or saturated members of the preferred fatty acid families.

The non-esterified fatty acids and monoglycerides are present in amounts which result in a molar ratio of from about 2:1 to about 1:2 (non-esterified fatty acid: monoglyceride).

In addition, the compositions have lysophosphatidylcholine, the fatty acid moiety of which has 14–18 carbon atoms and is preferably unsaturated. The fatty acid constituent of the lysophosphatidylcholine is preferably one of those listed above. The quantity of lysophosphatidylcholine in the composition is determined by the amount needed for enhanced solubilization of a drug to be administered in the composition and the amount needed for its role in translocation. In general, lysophosphatidylcholine choline comprises from about 1.0 mole % to about 30.0 mole % of the total composition. The fatty acids which comprise the compositions of this invention—whether as non-esterified fatty acids or as constituents of mono-glycerides or lysophosphatidylcholine—can all be the same or a number of different ones can be included.

Lipid formulations including the fatty acids, monoglycerides and lysophosphatidylcholine described above will swell in the presence of distilled water when heated and hand-shaken. Eventually, a gelatinous matrix is yielded that appears to be crystalline when viewed under a polarizing microscope. In the presence of 0.1 N HCl or pH 7.0 phosphate buffer, these lipid formulations do not appear to swell in the presence of distilled water when heated and hand-shaken, but remain as large oil/solid particles in these solutions. In contrast, these lipid formulations in the presence of distilled water and aqueous bile salts, with heat and hand-shaking, yield micron sized particles when viewed under a polarizing microscope. A conclusion that can be drawn from these observations is that the ionic species in the aqueous medium affect the size and constitution of particles formed from these lipid formulations. In particular, the anion types can significantly alter lipid particle formation, constitution and size.

It is known that, in addition to bile salts, the principal anion in the upper region of the small intestine is bicarbonate. It has been found that when this anion is present in sufficient quantities in the aqueous medium of the lipid formulations, submicron particles can be formed. The bicarbonate is incorporated in the compositions of the present invention by directly mixing the bicarbonate with the lipid components, or, preferably, by dissolving salts of this anion, such as sodium bicarbonate, potassium bicarbonate, etc., in the aqueous environment to which the previously mixed lipid components of the compositions have been placed. When the mixed lipid colloidal particles are formed by the shearing operation, bicarbonate is integrally included in the particulate form of the compositions.

If bile salts are additionally present in sufficient quantities in the aqueous environment, the already submicron particles can be even further reduced in size. Examples of bile salts that will reduce the size of the mixed lipid-bicarbonate colloidal particles are sodium taurocholate and sodium glycocholate. The bile salts can be added to the non-aqueous mixed lipid-bicarbonate mixture, or, preferably, are added to the aqueous environment in which the lipid components and bicarbonate have been combined. The bile salts then become incorporated in the colloidal particles of the compositions when these particles are formed by the shearing operation.

The compositions of this invention are preliminarily made according to the following method. The component lipids are weighed and mixed, with or without heat, to attain liquid homogeneity. When a drug is incorporated, it is added and dissolved, with or without heat, in the lipid mixture. A uniform state is indicated by the absence of any solids at the appropriate temperature for the mixture to be a liquid and by the absence of any schleiren. A schleiric effect will be more apparent at greater concentrations of the drug in the lipid mixture if it is included. The formulation is stable to several freeze-thaw cycles; the appearance of solids or schleirin may indicate instability of the formulation.

A second preliminary method of making the formulation involves dissolving the component lipids and drug, if it is incorporated, in a solvent or mixture of solvents and mixing to attain homogeneity. The solvents are removed, in vacuo or by other suitable methods. The criteria for a suitable formulation are the same as noted above.

A desired amount of an above preliminary formulation is placed in an aqueous environment. This aqueous environment is predominately water. Other substances can be present without altering the basic compositions. Examples of these other substances are pH buffering materials, amino acids, proteins, such as albumin or casein, and viscosity enhancers such as xanthine gums or gum arabic. The only criterion for the presence of these other substances is that they not substantially interfere with or alter the forces which cause the individual components of the composition to form the colloidal particles of the composition.

Bicarbonate is added to the aqueous environment by dissolving a desired amount of bicarbonate salt in the aqueous environment either before or after the preliminary formulation has been placed there.

The component lipid mixture in the aqueous environment is then subjected to shearing forces by an appropriate means. Typically, these shearing forces are achieved with a sonicator or a microfluidizer. The shearing operation is performed at an appropriate energy and for a time sufficient to yield homogeneous lipid-containing particles of the desired size. As noted in a below exemplification, the amount of bicarbonate relative to the amount of lipid formulation is important in determining the ultimate size of the mixed lipid-bicarbonate colloidal particles. Below a molar ratio of 1.4:1 (bicarbonate:mixed lipid formulation) the mixed lipid bicarbonate colloidal particle size will be larger than approximately 120 nm. Between a molar ratio of 1.4:1 and 7:1, the mixed lipid-bicarbonate colloidal particle size will be between approximately 120 nm and approximately 70 nm.

depending on the molar ratio of bicarbonate to mixed lipid formulation. The bicarbonate can be added gradually or all at one time as the shearing procedure is performed. Alternatively, the bicarbonate can be added before the shearing procedure is performed.

To obtain smaller submicron particles, bile salts at an appropriate molar ratio (bile salt:mixed lipid formulation) can be added to the aqueous medium before, concurrently, or after the bicarbonate is added. The molar ratios of bile salt to mixed lipid formulation as well as bicarbonate to mixed lipid formulation can be any independent value, provided each of them is at least about 1:1 (i.e., the bile salt concentration or the bicarbonate concentration should be at least the same as the mixed lipid concentration). That is, the bile salt:mixed lipid formulation molar ratio as well as the bicarbonate:mixed lipid formulation molar ratio can be independently changed, resulting in an accompanying change in the mixed lipid-bicarbonate-bile salt colloidal particle size. However, to achieve mixed lipid-bicarbonate-bile salt colloidal particles of 10 nm or less, the molar ratio of bile salt to mixed lipid formulation should be at least about 10:1 and the molar ratio of bicarbonate to mixed lipid formulation should be at least 7:1. Again, the bile salts can be added gradually or all at one time before or while the shearing operation is performed.

As previously noted, compositions of the present invention can also include a drug, which is any chemical agent or chemical substance which affects living processes. They include, but are not limited to, drugs administered for diagnostic, therapeutic or preventive purposes; lipophilic pro-drugs; nutrients, such as fat soluble vitamins, and other xenobiotics.

Biologically compatible surfactants can be added at any time to the aqueous medium containing the lipid formulation and bicarbonate (optionally also containing the bile salt). Examples of biologically compatible surfactants include TWEEN 20, TWEEN 80, etc. These surfactants can be added before or after the shearing operation.

The mixed lipid-bicarbonate or the mixed lipid-bicarbonate-bile salt colloidal particles are stable and can be stored under normal storage conditions. When a drug is incorporated in either of these compositions, the colloidal particles serve as a vehicle for transporting the drug to the intestinal mucosal cells following oral administration of the drug-containing particles to an individual. These drug-containing colloidal particles can be packaged, for example, in individual containers for oral administration of specific dosages of the incorporated drug. An individual simply opens the packaging container and swallows its contents to achieve the oral administration of the drug-containing colloidal particles.

Likewise, the mixed lipid-bicarbonate or the mixed lipid-bicarbonate-bile salt compositions can serve as a source of calories when administered without an incorporated drug. Again, an individual simply swallows the contents of a container that has a specific amount of the mixed lipid formulation to achieve oral administration of the desired composition.

The mixed lipid-bicarbonate or the mixed lipid-bicarbonate-bile salt compositions, with or without a constituent drug, also can be topically applied to the skin of an individual. Such application provides a source of lipids, and drug if included, to the skin surface for whatever purpose is desired.

The present invention is illustrated by the following examples which are not intended to be limiting of the invention.

EXAMPLE 1

Formation of Submicron Sized Particles of Lipid Formulations

The following lipids were mixed together to yield a non-aqueous lipid mixture: soy lysophosphatidylcholine (LPC), 18:1 monoolein monoglyceride (MG), and 18:1 oleic acid fatty acid (FA). The sources of these lipids were: Avanti Polar Lipids, 5001A Whitling Drive, Pelham, Ala. 35124 for LPC, and Nu-Chek-Prep, Inc., P. O. Box 295, Elysian, Minn. 56028 for MG and FA. The molar ratio of these lipid components was 1:3:3 for LPC:MG:FA. This non-aqueous lipid mixture was put into water at LPC concentrations ranging from $10^{-3}$ to 1 mM. Since the molar ratio of LPC:MG:FA was 1:3:3, the total lipid mixture molar concentrations also ranged from $10^{-3}$ to 1 mM in the water environment. These formulations were then subjected to probe sonication (Cole-Parmer, 4710 Series with a S&M 10 86 tip, 1.25 minutes at full power output). The surface tension (dynes/cm) of these mixed lipid formulations was measured by determining the time between drops. Using this technique, the critical micelle concentration of this mixed lipid formulation was found to be about 0.1 mM (See FIG. 1).

Figure 2:
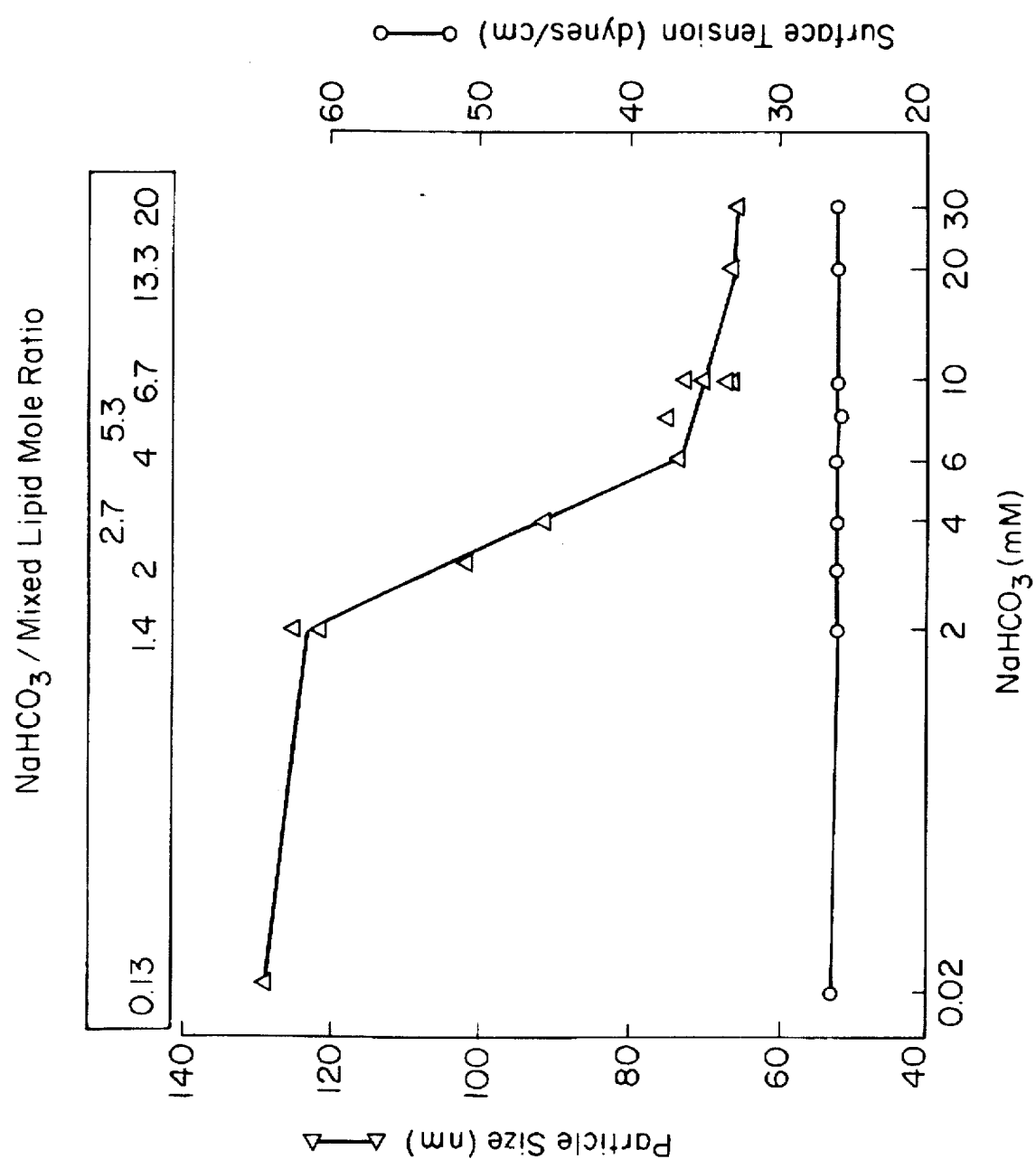
FIG. 2 is a graph showing the relationship between the particle size or surface tension of the mixed lipid formulation and the amount of sodium bicarbonate in the aqueous environment.

Particle sizes were measured of a 1.5 mM concentration of LPC (and also total lipid mixture) of the 1:3:3 LPC:MG:FA formulation in water after probe sonication was performed. The particle sizes were measured with either a Nicomp Analyzer or a Brookhaven Particle Sizer. After the initial probe sonication, the particle size was approximately 170 nm. Sodium bicarbonate, $NaHCO_3$, was incrementally added, sonication was continued and particle size was monitored. As the molar ratio of bicarbonate to lipid formulation (bicarbonate:lipid) approached 1.4:1, the particle size approached approximately 120 nm. When the bicarbonate:lipid molar ratio was increased to 7:1, the particle size decreased to approximately 70 nm. Between these bicarbonate:lipid molar ratios, intermediate size particles of the lipid formulation were observed (see FIG. 2). As the bicarbonate:lipid molar ratio was further increased, the particle size did not significantly change.

Figure 3:
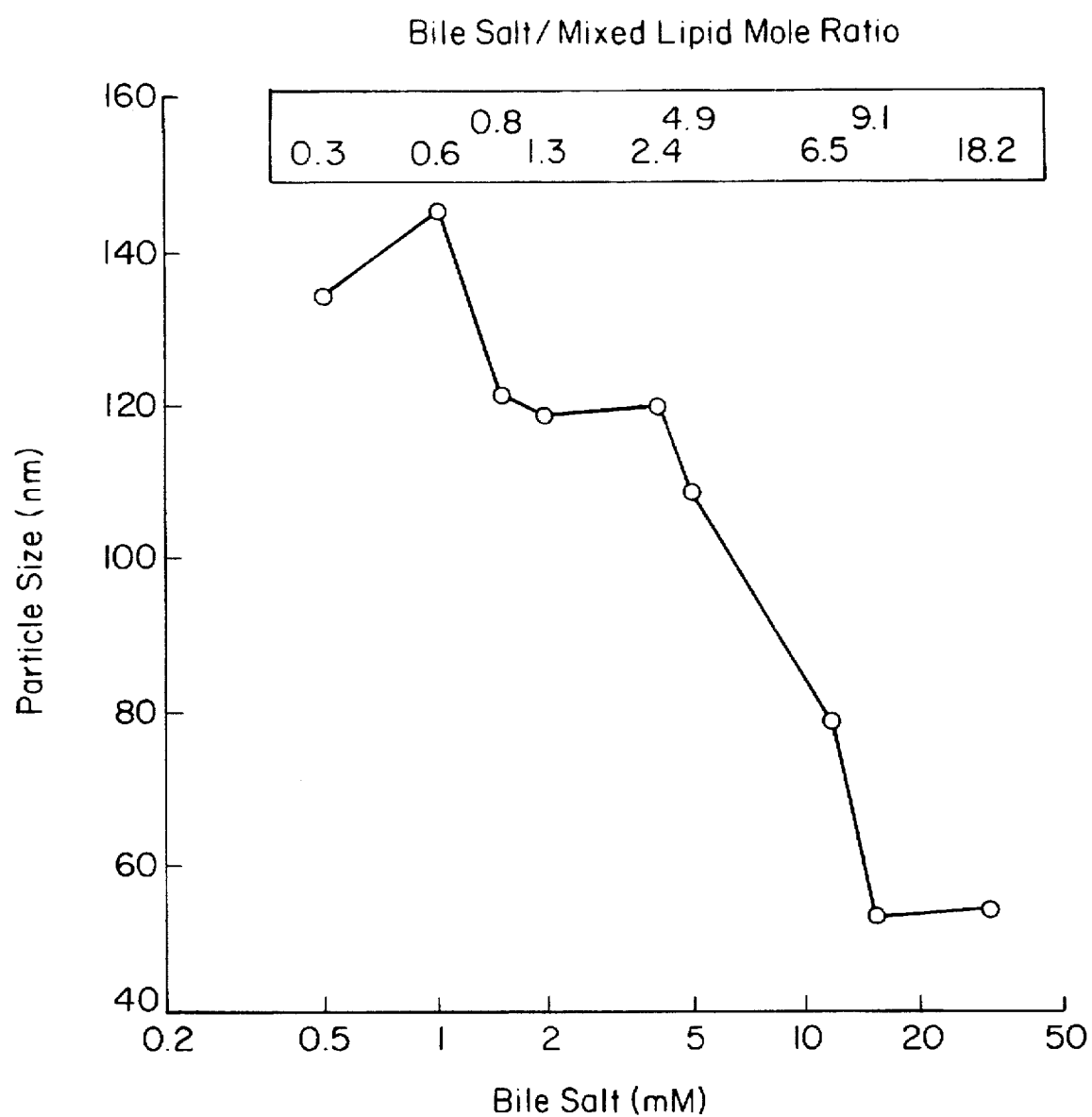
FIG. 3 is a graph showing the relationship between the particle size of the mixed lipid formulation and the amount of bile salt, sodium taurocholate, in the aqueous environment.

In another experiment, soy lysophosphatidylcholine, 18:1 monoolein monoglyceride, and 18:1 oleic acid fatty acid from the same sources as in the first experiment were mixed together to yield a non-aqueous lipid mixture with a molar ratio of 1:3:3 LPC:MG:FA. The non-aqueous lipid mixture was put into water so the LPC (and also total lipid mixture) molar concentration was about 1.7 mM. This formulation was then subjected to either probe sonication (Cole-Parmer sonicator) or shearing by action of a Microfluidizer (Model 110T, 2 passes at 70 psi). After the shearing operation, the particle size was approximately 150 nm for the 1:3:3 formulation. The bile salt, sodium taurocholate, was gradually added and shearing was continued. The particle size was monitored as the bile salt was added. The particle size was reduced to approximately 100 nm while the bile salts were in their monomeric state (i.e., less than about 5 mM) and the molar ratio of bile salt to mixed lipid was about 5:1. As more bile salt was added, the particle size for this formulation decreased to approximately 50 nm when the bile salts were primarily in their micellar state (i.e., greater than about 5 mM) and the molar ratio of bile salt to mixed lipid was about 9:1. Between these bile salt: mixed lipid molar ratios, intermediate size particles of the lipid formulations were observed (see FIG. 3).

Figure 4:
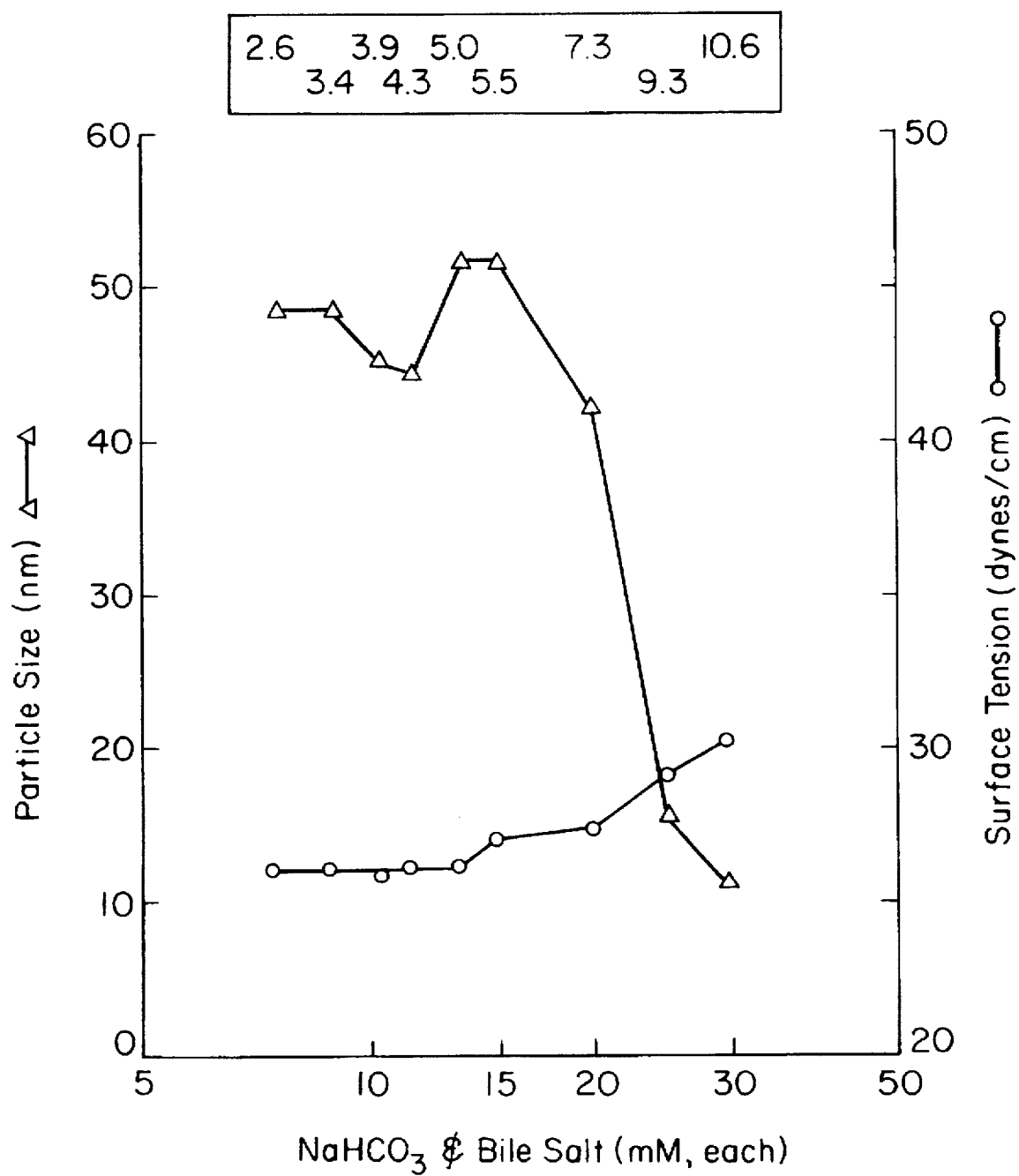
FIG. 4 is a graph showing the relationship between the particle size or surface tension of the mixed lipid formulation and the combination of bicarbonate and bile salt, sodium taurocholate.

When bicarbonate was added with sonication to the formulations of the latter experiment, the particle size was further reduced to approximately 10 nm or less as the bicarbonate:lipid molar ratio was increased to at least 7:1. When the bile salt, sodium taurocholate, was added with sonication to the formulation of the second experiment, the particle size was further reduced to approximately 10 nm or less as the bile salt:lipid molar ratio was increased to 10:1, i.e., as the bile salts reached their critical micellar concentration (achieving the micellar state). That is, when both the bicarbonate ion and bile salt reached their optimal concentrations for forming the smallest size particles of the lipid formulations, the particle size was approximately 10 nm or less (see FIG. 4, where the concentration of LPC, and also total lipid mixture, was about 2.7 mM for the 1:3:3 LPC-:MG:FA formulation).

EXAMPLE 2

Incorporation of Drugs in the Colloidal Particles

Figure 5:
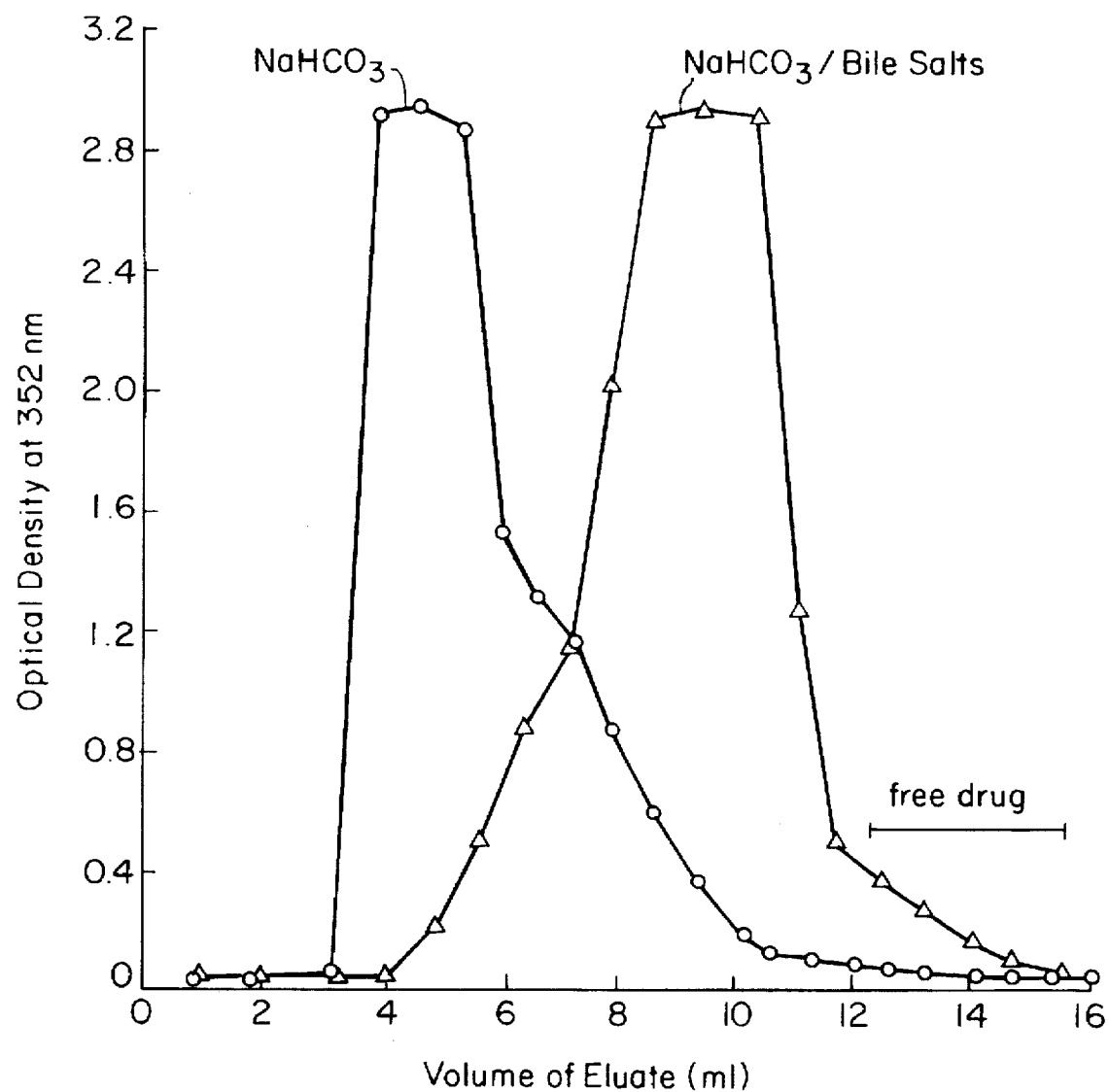
FIG. 5 is a graph showing the elution profiles from a Sepharose 4B column of the mixed lipid (fenretinamide)-bicarbonate, mixed lipid(fenretinamide)-bicarbonate-bile salt and of free fenretinamide.

Fenretinamide was formulated with the mixed lipid LPC-:MG:FA (1:3:3 molar ratio) using the solvent method of preparation. The molar concentration of fenretinamide was 0.8 with respect to LPC (and also total lipid mixture) in the mixed lipid(drug) formulation. This non-aqueous mixed lipid(drug) formulation was put into an aqueous environment so the LPC (and also total lipid mixture) concentration was about 1.3 mM. The aqueous environment contained either bicarbonate at a concentration of 12.5 mM (i.e. a molar ratio of about 10:1 for bicarbonate:(LPC in mixed lipid) or bicarbonate and bile salt at respective concentrations of 12.5 mM (i.e. molar ratios of 1:10:10 for LPC in mixed lipid:bicarbonate:bile salt). Colloidal particles of this mixed lipid (fenretinamide) with bicarbonate or with bicarbonate and bile salt were made by the method described in Example 1. This drug is hydrophobic in nature and tends to reside in the hydrocarbon region of the mixed lipid-bicarbonate or mixed lipid-bicarbonate-bile salt formulations. Upon size exclusion chromatography on a Sepharose 4B column, the drug remained associated with the mixed lipid-bicarbonate or with the mixed lipid-bicarbonate-bile salt particles (see FIG. 5). Free drug, i.e., without the presence of the particles, eluted from the column with a distinct elution profile in the region identified as 'free drug' in FIG. 5. The smaller size of the mixed lipid(drug)-bicarbonate-bile salt particles compared with the the mixed lipid(drug)-bicarbonate particles is noted from the longer retention before elution from the size exclusion column.

Figure 6:
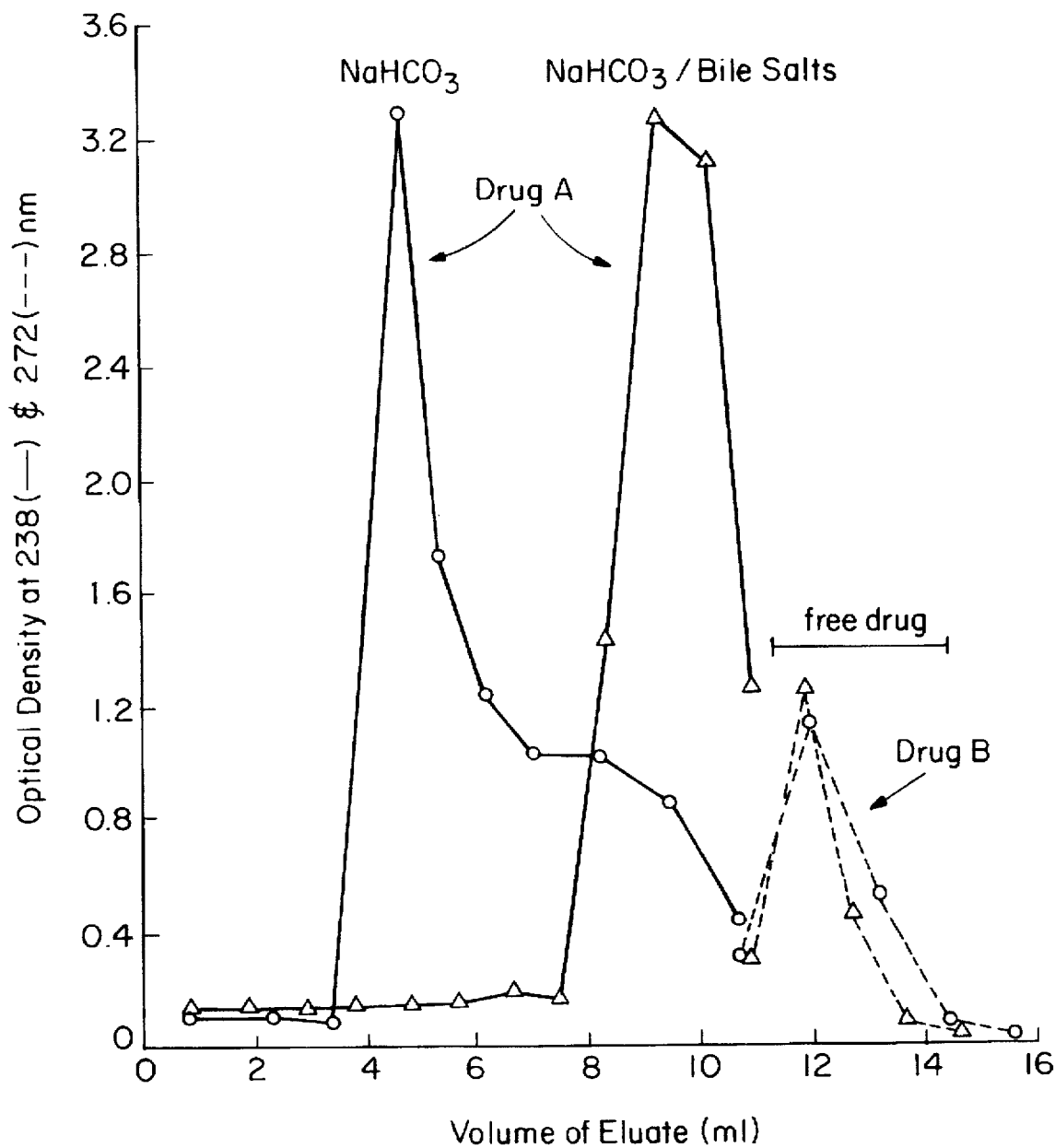
FIG. 6 is a graph showing the elution profiles from a Sepharose 4B column of the mixed lipid-bicarbonate formulation and the mixed lipid-bicarbonate-bile salt formulation containing diltiazem (Drug A) and hydrochlorothiazide (Drug B).

Diltiazem, a benzothiazepine, was formulated with the mixed lipid LPC:MG:FA (1:3:3 molar ratio) using the solvent method of preparation. Colloidal particles of this mixed lipid(diltiazem) formulation with either bicarbonate or bicarbonate and bile salt were made by the method described in the preceding experiment. This drug is hydrophobic in nature and tends to reside in the hydrocarbon region of the mixed lipid-bicarbonate formulations. Upon size exclusion chromatography on a Sepharose 4B column, the drug remained associated with the mixed lipid-bicarbonate particles as well as with the mixed lipid-bicarbonate-bile salt particles. Free drug, i.e. without the presence of the particles, eluted from the column with a distinct elution profile when compared with the drug associated with the mixed lipid-bicarbonate particles. (See Drug A and 'Free Drug' of FIG. 6).

In a separate experiment, hydrochlorothiazide (HCTZ) was formulated with the mixed lipid LPC:MG:FA (1:3:3 molar ratio) using the solvent method of preparation. This drug is not soluble per se with just monoglycerides and fatty acids. However, colloidal particles of this mixed lipid (HCTZ) formulation with bicarbonate were made by the method described in the first experiment of this Example. Size exclusion chromatography of these mixed lipid(HCTZ)-bicarbonate particles on a Sepharose 4B column showed the elution profile of HCTZ as free HCTZ. This indicates that HCTZ probably resides in the polar regions of the mixed lipid-bicarbonate formulations and becomes free drug when bicarbonate is present. Next, the mixed lipid(HCTZ) formulation and mixed lipid(diltiazem) formulation of the preceding experiment were mixed together at about a 1:5 weight ratio of the respective formulations. This 'super mixture' was then sonicated in either an aqueous bicarbonate solution or an aqueous bicarbonate-bile salt solution and the resulting materials were eluted by size exclusion chromatogrphy from a Sepharose 4B column. Mixed lipid (diltiazem)-bicarbonate colloidal particles or mixed lipid (diltiazem)-bicarbonate-bile salt colloidal particles (Drug A in FIG. 6) and free HCTZ (Drug B in FIG. 6) were eluted. These results show that with this technique of making mixed lipid(drug)-bicarbonate colloidal particles or mixed lipid(drug)-bicarbonate-bile salt colloidal particles, together with size exclusion chromatography, one can approximate the stability of mixed lipid-drug formulations to the milieu of the GI tract.

EXAMPLE 3

Skin Application of the Colloidal Particles

The mixed lipid formulation of Example 1 was additionally mixed with casein (1–2% casein by weight in the lipid mixture) or with visible or fluorescent dyes. Colloidal particles of mixtures with bicarbonate were made by the method described in Example 1. These colloidal particles were topically applied to the skin. Following this application, the colloid lipids that resided on the skin surface gave a desirable tactile sensability, e.g., softness, and repelled wetting of the skin surface with water. The colloidal particles that contained the visible or fluorescent dyes were solubilized from the skin surface by detergents.

Equivalents

Those skilled in the art will recognize, or be able to ascertain using no more than routine experimentation, many equivalents to the specific embodiments of the invention described herein. Such inventions are intended to be encompassed by the following claims.

I claim:

1. A composition for oral administration to an individual, to enhance absorption of a drug incorporated therein, comprising:
   a. at least one non-esterified fatty acid having 14–18 carbon atoms;
   b. at least one monoglyceride which is a monoester of glycerol and a fatty acid having 14–18 carbon atoms;
   c. lysophosphatidylcholine in which the fatty acid moiety has 14–18 carbon atoms;
   d. bicarbonate; and
   e. a drug;

wherein said fatty acids and monoglyceride together comprise from about 70.0 mole percent to about 99.0 mole percent of the lipid composition and the molar ratio of said fatty acids to said monoglycerides is from about 2:1 to about 1:2, and said lysophosphatidylcholine comprises from about 30.0 mole percent to about 1.0 mole percent of said lipid composition; and wherein the composition is in the form of colloidal particles in an aqueous environment.

2. The composition of claim 1 wherein said drug is a fat-soluble drug.

3. The composition of claim 2 wherein said drug is fenretinamide.

4. The composition of claim 2 wherein said drug is diltiazem.

5. The composition of claim 1 wherein the concentration of said lysophosphatidylcholine is at least 0.1 mM in said aqueous environment and the molar ratio of said bicarbonate to said lysophosphatidylcholine is greater than 1:1 in said aqueous environment.

6. The composition of claim 5 wherein the molar ratio of said bicarbonate to said lysophosphatidylcholine is greater than 1.4:1.

7. The composition of claim 6 wherein the molar ratio of said bicarbonate to said lysophosphatidylcholine is greater than 7:1.

8. The composition of claim 7 which additionally comprises bile salts wherein the molar ratio of said bile salts to said lysophosphatidylcholine in said aqueous environment is at least 10:1.

9. The composition of claim 8 wherein said bile salt is sodium taurocholate.

10. A method of delivering a drug comprising the oral administration of said drug in a composition comprised of:

(a) at least one non-esterified fatty acid having 14–18 carbon atoms;

(b) at least one monoglyceride which is a monoester of glycerol and a fatty acid having 14–18 carbon atoms;

(c) a lysophosphatidylcholine in which the fatty acid moiety has 14–18 carbon atoms;

(d) bicarbonate; and (e) a drug;

wherein the molar ratio of said fatty acids to said monoglycerides is from about 2:1 to about 1:2, and said lysophosphatidylcholine comprises from about 30.0 mole percent to about 1.0 mole percent of the total lipid in the composition; and wherein the composition is in the form of colloidal particles in an aqueous environment.

11. The method of claim 10 wherein said composition additionally comprises bile salts, wherein the molar ratio of said bile salts to said lysophosphatidylcholine is at least 10:1.

12. The method of claim 10 wherein the concentration of said lysophosphatidylcholine is at least 0.1 mM in said aqueous environment and the molar ratio of said bicarbonate to said lysophosphatidylcholine is greater than 1:1 in said aqueous environment.

13. The method of claim 12 wherein the molar ratio of said bicarbonate to said lysophosphatidylcholine is greater than 1.4:1.

14. The method of claim 13 wherein the molar ratio of said bicarbonate to said lysophosphatidylcholine is greater than 7:1.

15. The method of claim 14 which additionally comprises bile salts wherein the molar ratio of said bile salts to said lysophosphatidylcholine in said aqueous environment is at least 10:1.

16. The method of claim 15 wherein said bile salt is sodium taurocholate.

* * * * *